United States Patent [19]

Messina

[11] Patent Number: 4,965,070

[45] Date of Patent: Oct. 23, 1990

[54] DEER REPELLENT FORMULATION

[76] Inventor: James J. Messina, Cooper La., Chester, N.J. 07930

[21] Appl. No.: 407,271

[22] Filed: Sep. 14, 1989

Related U.S. Application Data

[63] Continuation-in-part of Ser. No. 215,982, Jul. 7, 1988, abandoned.

[51] Int. Cl.$^5$ .................... A01N 25/24; A01N 63/00; A01N 65/00
[52] U.S. Cl. ................. 424/581; 424/195.1; 424/405; 424/407
[58] Field of Search .............. 424/95, 195.1, 405, 424/407

[56] References Cited

U.S. PATENT DOCUMENTS

| | | | |
|---|---|---|---|
| 3,980,773 | 9/1976 | Oh et al. | 424/95 |
| 4,169,902 | 10/1979 | De Long | 424/81 |
| 4,388,303 | 6/1983 | Allan | 424/162 |
| 4,455,304 | 6/1984 | Yaralian | 424/195.1 |

*Primary Examiner*—Jacqueline Stone
*Assistant Examiner*—Jean C. Witz
*Attorney, Agent, or Firm*—Ribis, Graham & Curtin

[57] ABSTRACT

A deer repellent formulation for warding off a deer from a plant is provided. The deer repellent formulation includes, a volume of water; 12 fluid ounces of thiram in a water solution of 42% by volume of thiram, per gallon of the water; 2 whole chicken eggs per gallon of water; 2 ounces by volume of liquid hot sauce per gallon of water; green color dye in a sufficient quantity per gallon of the water to provide a plant-like green color of the formulation; and a liquid adhesive in sufficient quantity per gallon of the water to provide a desired stickiness on plants of the formulation.

3 Claims, No Drawings

DEER REPELLENT FORMULATION

The present invention relates to a deer repellent formulation, and more particularly to a deer repellent formulation which contains thiram as an essential ingredient.

This application is a continuation-in-part application of U.S. application Ser. No. 215,982, filed July 7, 1987; now abandoned.

BACKGROUND OF THE INVENTION

U.S. Pat. No. 1,871,949 discloses a composition of matter and the process of preparing that matter for use as an insect and rodent repellant. The patent teaches of a composition created by mixing oil of peppermint, sodium benzoate, sulfonethylmethane, animal glue, wood alcohol and water.

This composition when placed on the fibrous material hardens and sets firmly on the material. This composition will repel or kill insects. The problem with this patent is that it is not fully effective in repelling animals.

U.S. Pat. No. 2,212,701 relates to a plant spray insecticide. This patent teaches a composition of a glucose syrup, a neutral soap, sodium benzoate and water. The composition is mixed together and sprayed on plant life to kill insects and prevent the hatching of their eggs. The problem with this patent is that it is directed towards killing insects and not repelling animals.

U.S. Pat. No. 2,937,147 relates to a composition of germicidal detergents and a process for preparing that composition of detergents. This comprises a thorium sulfide compound that has each thorium nitrogen atom fully substituted with aliphatic groups and a peroxide. The patent teaches of a composition that is used as a soap that reduces bacteria from skin. This patent is directed towards killing human bacteria and not towards an animal repellant.

U.S. Pat. No. 3,060,084 relates to a readily dispersed pesticidal concentrate. This patent teaches a composition of a polycarboxylated hydrocarbon polymer acting as a suspension agent, a dispersing agent, water-insoluble pesticide and water. This mixture is then ground with and sheared to obtain its final rheological properties. This patent is directed towards ensuring the pesticide particles are readily dispersed in the pesticide spray medium and will not precipitate from the mixture.

U.S. Pat. No. 4,169,902 of DeLong teaches water for the spray medium, and thiram for a repellent. DeLong does not teach using chicken eggs, nor using hot sauce.

U.S. Pat. No. 4,388,303 of Allan teaches a formulation to be buried below ground in the soil around a seedling. Allan does not teach or suggest using water for an above-ground foliage spray medium, that is, using a relatively large percentage (68% to 90%) of the water in the formulation for such purpose. The only significance teaching of Allan is in his brief mention of assumed prior art at column 1, lines 39-54. Allan does not refer to any prior art patents or prior art publications, which contain his assumed prior art teaching. Allan also does not teach using hot sauce (pepper particles) for an animal throat irritant repellent or nasal-irritant repellent.

U.S. Pat. No. 3,962,425 of Oita et al teaches an animal repellent formulation including putrefied fish or beef. Oita et al does not teach the inclusion of a large percentage of a water medium, and does not teach the inclusion of a hot sauce (pepper particles) or a like throat-irritant material, and does not teach the inclusion of thiram, in the formulation.

U.S. Pat. No. 631,738 of Dowie et al teaches a non-poisonous rat-repellent dusting powder including pepper particles, a powder medium for floating the powder particles through the air, and hellebore. Dowie et al does not teach or suggest a water medium, nor thiram, nor chicken eggs.

U.S. Pat. No. 4,455,304 of Yaralian teaches a bird repellent formulation including, a water medium (about 98% wt.), pepper particles about 0.2% wt.).

OBJECTS OF THE INVENTION

It is an object of the present invention to provide a more fully effective deer repellent.

A further objective of this invention is to provide a more fully effective deer repellent that will adhere to surfaces which are exposed to rain and snow.

A further objective of this invention is to provide a more fully effective deer repellent that is cheaply produced.

A further objective of this invention is to provide a more fully effective deer repellent that can be applied indoors.

A further objective of this invention is to provide a more fully effective deer repellent that is made of easily obtainable items.

A further objective of this invention is to provide a more fully effective deer repellent that is easily applied to the surface to be protected.

Still another objective of this invention is to provide a more fully effective deer repellent that can be colored with a coloring dye so as to blend in with a plant's color.

These and still further objectives will become apparent hereinafter.

SUMMARY OF THE INVENTION

According to the present invention, a deer repellent formulation is provided. This formulation comprises approximately by volume: 68 to 90% water, 60 to 10% thiram which is 42% by volume in water solution, 0.5 to 2% chicken eggs, 1 to 2% liquid hot sauce such as that sold under the trademark GOYA, which is a mixture of hot perrper, tabasco peppers, vinegar and salt, 0.5 to 2% coloring dye such as that sold under the trademark "Greenzit" and 2 to 16% adhesive such as that sold under the trademark "Nu-Film-P." The term "deer" is intended to mean the North American deer, and animals having a common ancestor thereto.

DESCRIPTION OF THE PREFERRED EMBODIMENT

Thiram is the coined common name for the chemical tetraethylthiuram disulfide with the formula $C_6H_{12}N_2,4$ and is commonly used as a fungicide and as a seed disinfectant. It is packaged as 42% by volume in water solution. The advantage of using a fungicide is that it prevents the growth of fungus on the repellent mixture so as to prolong the length of its use.

The following mixture must be thoroughly stirred and is best accomplished using an electric stirrer. A stainless steel mixing container is also preferred.

Thiram is mixed with water to produce a 68 to 90% water solution. Two whole chicken eggs are separated from their shells and added to the mixture and account for 0.5% to 2% of the mixture. The eggs act as a deterrent agent.

Liquid hot sauce like that sold under the trademark Goya is stirred into this mixture as 1 to 2% by volume. Hot pepper other than Goya brand can be used and will be equally effective. Hot pepper powder is used because when an animal sniffs a surface that has been treated with the invention, inhalation of one or more pepper particles occurs. This inhalation causes momentary irritation to the respiratory system of the animal and causes the animal to retreat from the treated surface.

A coloring dye can then be mixed in the solution if the animal repellent is to be used on plants. Any green coloring dye that is like Greenzit is equally effective. The plant coloring comprises 0.5 to 2% by volume of the total mixture.

The last ingredient added is an adhesive like that sold under the trademark "Nu-Film-P". Other liquid adhesives can also be used. These account for 2 to 16% of the mixture. The adhesive can be added if the repellent mixture is to be used outdoors on a surface that is exposed to rain or snow.

EXAMPLE I

The deer repellent formulation in the preferred embodiment for outdoor application is shown below:
- 128 fluid ounces of water;
- 12 fluid ounces of thiram;
- 2 chicken eggs;
- 2 ounces by volume of liquid hot sauce;
- green coloring dye in an amount sufficient to produce desired color; and
- adhesive in a quantity sufficient to adhere to the plant.

EXAMPLE II

The deer repellent formulation in the preferred embodiment for indoor applications is shown below:
- 128 fluid ounces of water;
- 12 fluid ounces of thiram;
- 2 chicken eggs; and
- 2 ounces by volume of liquid hot sauce.

EXAMPLE III

The ranges of material for the deer repellent formulation in the preferred embodiment:

| Material | Percentaoe by Volume |
|---|---|
| water | 68 to 90% |
| thiram | 6 to 10% |
| chicken eggs | 0.5 to 2% |
| liquid hot sauc | 1 to 2% |
| coloring dye | 0.5 to 2% |
| adhesive | 2 to 16% |

What is claimed is:

1. A deer repellent formulation consisting essentially of by volume:
   - 68 to 90% water
   - 6 to 10% thiram
   - 0.5 to 2% chicken eggs
   - 1 to 2% liquid hot sauce
   - 0.5 to 2% coloring dye; and
   - 2 to 16% adhesive.

2. A deer repellent formulation consisting essentially of by volume:
   - 84% water;
   - 8% thiram;
   - 1% chicken eggs
   - 1% liquid hot sauce;
   - 1% coloring dye; and
   - 5% adhesive.

3. A method of repelling deer that comprises mixing 128 fluid ounces of water, 12 fluid ounces thiram, 2 chicken eggs and 2 ounces by volume of liquid hot sauce and applying said total mixture to a surface where protection is sought from deer.

* * * * *